United States Patent
Arvidsson et al.

(10) Patent No.: US 9,889,237 B2
(45) Date of Patent: Feb. 13, 2018

(54) MEDICAL DEVICE HAVING A SURFACE COMPRISING NANOPARTICLES

(71) Applicant: DENTSPLY INTERNATIONAL INC., York, PA (US)

(72) Inventors: Anna Arvidsson, Göteborg (SE); Ingela Mattisson, Torslanda (SE); Elisabet Ahlberg, Västra Frölunda (SE); Johanna Löberg, Göteborg (SE)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 13/875,355

(22) Filed: May 2, 2013

(65) Prior Publication Data

US 2013/0302427 A1  Nov. 14, 2013

Related U.S. Application Data (60) Provisional application No. 61/645,746, filed on May 11, 2012.

(30) Foreign Application Priority Data

May 11, 2012  (EP) .................................... 12167724

(51) Int. Cl.

| | | |
|---|---|---|
| A61L 27/06 | (2006.01) | |
| A61L 27/30 | (2006.01) | |
| A61K 6/02 | (2006.01) | |
| A61L 31/02 | (2006.01) | |
| A61K 6/00 | (2006.01) | |
| A61L 27/02 | (2006.01) | |
| A61L 31/16 | (2006.01) | |
| A61C 8/00 | (2006.01) | |

(52) U.S. Cl.
CPC .............. *A61L 31/028* (2013.01); *A61C 8/00* (2013.01); *A61K 6/0073* (2013.01); *A61L 27/02* (2013.01); *A61L 27/06* (2013.01); *A61L 27/30* (2013.01); *A61L 27/306* (2013.01); *A61L 31/16* (2013.01); *A61C 8/0013* (2013.01); *A61L 2400/12* (2013.01); *A61L 2430/02* (2013.01); *A61L 2430/12* (2013.01); *A61L 2430/14* (2013.01); *F04C 2270/0421* (2013.01)

(58) Field of Classification Search
None
See application file for complete search history.

(56) References Cited

U.S. PATENT DOCUMENTS

| | | | |
|---|---|---|---|
| 2001/0055622 A1* | 12/2001 | Burrell et al. ................. | 424/600 |
| 2003/0165556 A1 | 9/2003 | Bechert et al. | |
| 2004/0021289 A1 | 2/2004 | Wu | |
| 2005/0025797 A1 | 2/2005 | Wang et al. | |
| 2006/0204738 A1 | 9/2006 | Dubrow et al. | |
| 2009/0017087 A1* | 1/2009 | Byon ................... | A61F 2/30767 424/422 |
| 2010/0196440 A1* | 8/2010 | Stark et al. .................... | 424/426 |
| 2012/0128932 A1* | 5/2012 | Veith ..................... | A61L 27/047 428/141 |
| 2012/0214132 A1* | 8/2012 | Takahashi et al. ........... | 433/173 |

FOREIGN PATENT DOCUMENTS

| | | | | |
|---|---|---|---|---|
| EP | | 1430913 A1 | 6/2004 | |
| WO | | WO92013491 A1 * | 8/1992 | |
| WO | | 2001080920 A2 | 11/2001 | |
| WO | | 2006060033 A1 | 6/2006 | |
| WO | | 2007053581 A2 | 5/2007 | |
| WO | WO | 2007053581 A2 * | 5/2007 | ............. A23K 1/175 |
| WO | | 2008049242 A1 | 5/2008 | |
| WO | | 2011012213 A2 | 2/2011 | |
| WO | WO | 2011012213 A2 * | 2/2011 | ........... A61L 27/047 |

OTHER PUBLICATIONS

William B. Jensen—"The Place of Zinc,Cadmium & Mercury in the Periodic Table",Journal of Chemical Education, Aug. 8, 2003,(Aug. 8, 2003) pp. 952-960.
European Search Report, Application No. 12167724.9, Published Feb. 12, 2013.
International Search Report , Application No. 2013/058914, Published Apr. 29, 2013.
International Written Opinion, Application No. 2013/058914, Published Apr. 29, 2013.
Zareenabbas,Christophe Labbez,Sture Nordholm, & Elisabet Ahlberg., Journal of Physical Chemistry. C 2008, 112, 5715-5723.
Yu etal, Journal of American Chemistry Soc (2001) 123: 9198-9199.
Krajczyk et al, Journal of Microscopy (2006) 223: 231-233.
Li et al, Mater Chem Phys (2006) 99: 174-180.
Lv et al, Journal of Haardous Material (2009) 161: 396-40.
Nyk et al, Material Sci Semicon Proces (2005) 8: 511-514.
M. Yasuyuki, K. Kunihiro, S. Kurissery, N. Kanavillil, Y. Sato, Y. Kikuchi. Biofouling 26 (2010) 851-858.

\* cited by examiner

*Primary Examiner* — H. S Park
(74) *Attorney, Agent, or Firm* — Douglas J. Hura; David A. Zdurne; Leana Levin (57) ABSTRACT

A medical device has a surface intended for contact with living tissue, wherein the surface comprises nanoparticles comprising a non-toxic post-transition metal such as gallium and/or bismuth, said nanoparticles having an average particle size of 500 nm or less. The nanoparticles may provide an antimicrobial effect, and thus the risk for infection may be reduced.

7 Claims, 3 Drawing Sheets

MEDICAL DEVICE HAVING A SURFACE COMPRISING NANOPARTICLES

CROSS-REFERENCE TO RELATED APPLICATIONS

This patent application claims the benefit of and priority to EP Application Ser No. 12167724.9, filed on May 11, 2012 and U.S. Provisional Patent Application Ser. No. 61/645,746, filed on May 11, 2012, which are herein incorporated by reference for all purposes.

FIELD OF THE INVENTION

The present invention relates to the field of medical devices intended for contact with living cells or tissue, in particular implants intended for implantation into living tissue, and to methods of producing such medical devices.

BACKGROUND OF THE INVENTION

For any type of medical device intended for contact with living tissue, biocompatibility is a crucial issue. The risk for foreign body reaction, clot formation and infection, among many other things, must be addressed and minimized in order to avoid adverse effects, local as well as systemic, which may otherwise compromise the health of the patient and/or lead to failure of the device. This is particularly the case for permanent implants.

Healing or regeneration of tissue around an implant is often vital in order to secure the implant and its functionality, in particular for long-term implants. This is especially important for load-bearing implants such as dental or orthopedic implants.

Dental implant systems are widely used for replacing damaged or lost natural teeth. In such implant systems, a dental fixture (screw), usually made of titanium or a titanium alloy, is placed in the jawbone of the patient in order to replace the natural tooth root. An abutment structure is then attached to the fixture in order to build up a core for the part of the prosthetic tooth protruding from the bone tissue, through the soft gingival tissue and into the mouth of the patient. On said abutment, the prosthesis or crown may finally be seated.

For dental fixtures, a strong attachment between the bone tissue and the implant is necessary. For implants intended for contact with soft tissue, such as abutments which are to be partially located in the soft gingival tissue, also the compatibility with soft tissue is vital for total implant functionality. Typically, after implantation of a dental implant system, an abutment is partially or completely surrounded by gingival tissue. It is desirable that the gingival tissue should heal quickly and firmly around the implant, both for medical and aesthetic reasons. A tight sealing between the oral mucosa and the dental implant serves as a barrier against the oral microbial environment and is crucial for implant success. This is especially important for patients with poor oral hygiene and/or inadequate bone or mucosal quality. Poor healing or poor attachment between the soft tissue and the implant increases the risk for infection and peri-implantitis, which may ultimately lead to bone resorption and failure of the implant.

There are several strategies for increasing the chances of a successful implantation of a medical device, for example enhancing the rate of new tissue formation and/or, in instances where tissue-implant bonding is desired, enhancing the rate of tissue attachment to the implant surface, or by reducing the risk for infection. Enhancement of new tissue formation may be achieved for example by various surface modifications and/or deposition of bioactive agents on the surface.

The risk of infection in connection with dental implants is today primarily addressed by preventive measures, such as maintaining good oral hygiene. Once a biofilm is formed on the surface of a dental implant, it is difficult to remove it by applying antibacterial agents. In the case of infection in the bone or soft tissue surrounding a dental implant (peri-implantitis), mechanical debridement is the basic element, sometimes in combination with antibiotics, antiseptics, and/or ultrasonic or laser treatment.

Hence, there is a need in the art for improved strategies for treating or preventing infection, not only in connection with dental implants but any type of implant or other medical device intended for contact with living tissue.

SUMMARY OF THE INVENTION

It is an object of the present invention to at least partially overcome the problems of the prior art. In particular it is an object of the invention to provide a medical device which decreases the risk for detrimental infection by microbes.

In one aspect, these and other objects are achieved by a medical device having a surface intended for contact with living tissue, wherein the surface comprises nanoparticles comprising a non-toxic post-transition metal, such as gallium and/or bismuth, the nanoparticles having an average particle size of 500 nm or less. The presence of the non-toxic post-transition metal provides an antibacterial property. Hence, the risk for infection at the implantation site may be reduced. Furthermore, a nanoparticle coating may provide desirable surface characteristics in terms of electrochemical properties and surface roughness, and since the nanoparticles are small, the porosity of the nanoparticle coating is limited, which reduces the risk for penetration of microbes into the surface. In addition, it is believed that a coating of nanoparticles comprising a non-toxic post-transition metal may be adapted e.g. with respect to layer thickness, to provide a particular colored appearance, which may be highly desirable for certain applications, such as dental implants.

The term "post-transition metal" generally refers to metal elements found in groups 13-16 and periods 3-6 of the periodic table. Post-transition metals of groups 13-15 and periods 3-6 are preferred.

In embodiments of the invention, the post-transition metal used is non-toxic. As used herein, "non-toxic" means that the substance (e.g. a compound or element) in question does not damage mammalian cells at concentrations that have a lethal effect on bacterial cells.

Furthermore, the post-transition metal used in the present invention typically has an antimicrobial or antibacterial effect. Post-transition metals that are considered to have some antimicrobial or antibacterial effect (including any oligodynamic effect) include at least gallium, tin, lead, and bismuth.

In view of the above, the invention may employ at least one non-toxic, antimicrobial post-transition metal, which may be selected from gallium and bismuth.

In embodiments of the invention, the nanoparticles may comprise a compound of a non-toxic post-transition metal. As used herein, the term "compound of a post-transition metal" refers to a chemical entity comprising at least one post-transition metal and at least one additional element. Non-limiting examples of such compounds include oxides comprising post-transition metal, nitrides comprising post-transition metal, alloys of at least one post-transition metal, and salts comprising post-transition metal. The compound may comprise two or more post-transition metals. The term "compound(s) of a post-transition metal" is intended to also refer to compounds incorporating one or more other metals, in particular biocompatible metals such as titanium, in addition to the one or more post-transition metal(s). The non-toxic post-transition metal and the at least one additional element may be joined by covalent bonding or ionic bonding.

In embodiments of the invention, the non-toxic post-transition metal is selected from bismuth and gallium. Compound(s) of the non-toxic post-transition metal may thus be selected from bismuth compound(s) and gallium compound(s).

In embodiments of the invention, the nanoparticles may comprise a gallium compound. The gallium compound may be selected from the group consisting of gallium oxide, gallium nitride, metal oxides comprising gallium and metal nitrides comprising gallium. In embodiments of the invention, the nanoparticles may comprise elemental bismuth or a bismuth compound. In particular, the bismuth compound is selected from the group consisting of bismuth oxide, bismuth nitride, metal oxides comprising bismuth and metal nitrides comprising bismuth.

The term "gallium compound" also includes compounds including one or more other metals in addition to gallium, in particular titanium and/or bismuth. Thus, gallium-titanium oxides, gallium-titanium nitrides etc are included within the definition "gallium compound". By "metal oxides comprising gallium" is meant an oxide optionally comprising one or more additional element(s) other than gallium and oxygen, for example a metal such as titanium. Examples of "oxides comprising gallium" include gallium oxide, gallium-titanium oxide, gallium-bismuth oxide, etc.

By analogy, the term "bismuth compound" refers to a chemical entity comprising bismuth and at least one additional element. Non-limiting examples of bismuth compounds include bismuth oxide, bismuth nitride, metal oxides comprising bismuth and metal nitrides comprising bismuth. The term "bismuth compound" also includes compounds incorporating other metals in addition to bismuth, in particular titanium and/or gallium. Thus, bismuth-titanium oxides, bismuth-titanium nitrides etc are included within the definition "bismuth compound". Furthermore, by "metal oxides comprising bismuth" is meant an oxide optionally comprising one or more additional element(s) other than bismuth and oxygen, for example a metal such as titanium or gallium. Examples of "oxides comprising bismuth" thus include bismuth oxide as well as bismuth-titanium oxide, gallium-bismuth oxide, etc.

In embodiments of the invention, the nanoparticles may have an average particle size of 300 nm or less, 250 nm or less, 200 nm or less, e.g. 100 nm or less, such as 50 nm or less, 30 nm or less, or 25 nm or less.

In embodiments of the invention, the surface may further comprise nanoparticles of titanium dioxide having an average particle size of 100 nm or less, for example 50 nm or less, such as 30 nm or less. Titanium oxide is an inert, biocompatible material and a surface layer comprising titanium dioxide nanoparticles may provide desirable surface characteristics in terms of electrochemical properties and surface roughness In embodiments of the invention, the nanoparticles may form a layer. The layer may have a thickness in the range of from 8 nm to about 1 μm, typically from 50 nm to 500 nm, for example from 100 nm to 400 nm. The layer may be a monolayer of the nanoparticles. Furthermore, the layer may be a continuous layer of the nanoparticles. Typically, the layer may completely cover the surface of an underlying substrate. The nanoparticles may be evenly spread throughout the layer.

Typically, the medical device comprises a substrate having a surface onto which the nanoparticles are applied. In embodiments of the invention, the substrate may comprise a metal or an alloy, for example titanium, zirconium, hafnium, vanadium, niobium, tantalum, cobalt or iridium, or an alloy thereof, in particular titanium or a titanium alloy. In embodiments of the invention, the substrate may comprise a ceramic material, which may be selected from titanium oxide, titanium nitride, zirconium oxide, and combinations thereof.

In embodiments of the invention, a part of the substrate that is in contact with the nanoparticles may comprise titanium oxide, in particular native titanium oxide.

In embodiments of the invention the substrate may be non-bioresorbable.

Typically, the medical device is intended for implantation at least partially into living tissue. For example, the medical device may be a dental implant, such as a dental fixture intended to be inserted at least partially into living bone tissue, or a dental abutment, intended to be in contact with living soft tissue. Alternatively, the medical device may be an orthopedic implant. In other embodiments, the medical device may be a bone anchored hearing device or a part thereof.

In embodiments of the invention, the medical device may be a stent. In other embodiments, the medical device may be a shunt.

In another aspect, the invention provides a method of producing a medical device, the method comprising the steps of:
a) providing a substrate having a surface;
b) providing a dispersion of nanoparticles comprising a non-toxic post-transition metal, such as gallium and/or bismuth, the nanoparticles being dispersed in a solvent, the nanoparticles having an average particle size of less than 500 nm, e.g. less than 100 nm or less than 50 nm; and
c) applying the dispersion of nanoparticles onto the surface of the substrate.

The nanoparticles may be completely dispersed in the solvent. Such a monodispersion gives improved control of the coating procedure and allows the application of a continuous, homogeneous layer, even a monolayer, of nanoparticles on the surface.

For example, the dispersion may be applied onto the surface by spin coating.

In embodiments of the invention the surface of the substrate body prior to step c) may have been subjected to a roughening surface treatment, such as abrasive blasting and/or chemical etching.

In embodiments of the invention, the method may further comprise one or more steps of allowing the solvent to evaporate, and/or sintering the nanoparticles. Sintering of a layer of the nanoparticles may improve the attachment of the nanoparticles to the substrate. Sintering of the nanoparticles may result in a ceramic or ceramic-like layer.

In a further aspect, the invention provides a method of implanting a medical device into the living body of a human or animal, the method comprising:

a) providing a medical device as described above; and
b) implanting the medical device into the living body of a human or animal, wherein the medical device is positioned such that at least part of the surface comprising nanoparticles comprising a non-toxic post-transition metal is in contact with living tissue.

Implantation of the present medical device into living tissue, with the surface comprising the nanoparticles contacting the tissue, may reduce the risk for microbial, in particular bacterial, infection of the tissue. Avoiding infection will increase the chances of a successful implantation, especially for prolonged or long-term implantation periods.

It is noted that the invention relates to all possible combinations of features recited in the claims.

DETAILED DESCRIPTION OF THE INVENTION

According to the present invention, nanoparticles comprising a non-toxic post-transition metal, such as gallium and/or bismuth, for example in the form of oxide(s) or nitride(s), may be applied onto the surface of a medical device, to yield a surface having antimicrobial properties. The surface of the medical device presenting the nanoparticles is typically a surface intended for contact with living tissue.

The term "post-transition metal" generally refers to metal elements found in groups 13-16 and periods 3-6 of the periodic table. Usually, aluminium, gallium, indium, thallium, tin, lead, bismuth and polonium are regarded as post-transition metals. In contrast, transition metals are formed of group 3-12 elements. Germanium and antimony are considered not as post-transition metals, but metalloid elements.

Group 16 of the periodic table only contains one post-transition metal: polonium, which is toxic. Hence, in the present invention, post-transition metals of groups 13-15 and periods 3-6 are preferred.

In embodiments of the invention, the post-transition metal used is non-toxic.

As used herein, "non-toxic" means that the substance (e.g. a compound or element) in question does not damage mammalian cells at concentrations that have a lethal effect on bacterial cells.

Examples of post-transition metals that are toxic include thallium (Tl), lead (Pb) and polonium (Po). Other post-transitional metals (e.g. indium (In) and tin (Sn)) may be considered non-toxic in the pure metal form, but may be toxic in other forms or when they form compounds with other elements.

The non-toxic post transition metal used in the present invention is typically non-toxic when present in elementary form, and/or as metal ions, and/or as one of the exemplary compounds given herein.

Furthermore, the post-transition metal used in the present invention typically has an antimicrobial or antibacterial effect. Elements known to be associated with antimicrobial properties include e.g. Ga, Bi, Ag, Zn, Au, Pt, Pd, Ir, Cu, Sn, and Sb. Post-transition metals that are considered to have some antimicrobial or antibacterial effect (including any oligodynamic effect) include at least gallium (Ga), tin (Sn), lead (Pb), and bismuth (Bi).

In view of the above, the medical device according to embodiments of the invention may employ at least one non-toxic, antimicrobial post-transition metal, which may be selected from gallium and bismuth.

Gallium has been used in medicine at least since the 1940's, primarily as a radioactive agent for medical imaging. The antibacterial properties of gallium have been investigated in several studies. Gallium acts by disrupting iron metabolism. It may be assumed that gallium is also effective against other microbes, e.g. fungi such as yeasts or moulds.

Bismuth is known to possess antibacterial activity. Bismuth compounds were formerly used to treat syphilis, and bismuth subsalicylate and bismuth subcitrate are currently used to treat peptic ulcers caused by *Helicobacter pylori*. The mechanism of action of this substance is still not well understood. Bibrocathol is an organic bismuth-containing compound used to treat eye infections, and bismuth subsalicylate and bismuth subcarbonate are used as ingredients in antidiarrheal pharmaceuticals.

Directive 2007/47/ec defines a medical device as: "any instrument, apparatus, appliance, software, material or other article, whether used alone or in combination, including the software intended by its manufacturer to be used specifically for diagnostic and/or therapeutic purposes and necessary for its proper application, intended by the manufacturer to be used for human beings". In the context of the present invention, only medical devices intended for contact with living tissue are considered, that is, any instrument, apparatus appliance, material or other article of physical character that is intended to be applied on, inserted into, implanted in or otherwise brought into contact with the body, a body part or an organ. Furthermore, in the context of the present invention, the body, body part or organ may be that of a human or animal, typically mammal, subject. Typically however the medical device is intended for human subjects. Medical devices included within the above definition are for example implants, catheters, shunts, tubes, stents, intrauterine devices, and prostheses.

In particular, the medical device may be a medical device intended for implantation into living tissue or for insertion into the body or a body part of a subject, including insertion into a bodily cavity.

The present medical device may be intended for short-term, prolonged or long-term contact with living tissue. By "short-term" is meant a duration of less than 24 hours, in accordance with definitions found in ISO 10993-1 for the biological evaluation of medical devices. Furthermore, "prolonged", according to the same standard, refers to a duration of from 24 hours up to 30 days. Accordingly, by the same standard, by "long-term" is meant a duration of more than 30 days. In some embodiments of the present invention the medical device of the invention may be a permanent implant, intended to remain for months, years, or even life-long in the body of a subject.

As used herein the term "implant" includes within its scope any device of which at least a part is intended to be implanted into the body of a vertebrate animal, in particular a mammal, such as a human. Implants may be used to replace anatomy and/or restore any function of the body.

Generally, an implant is composed of one or several implant parts. For instance, a dental implant usually comprises a dental fixture coupled to secondary implant parts, such as an abutment and/or a restoration tooth. However, any device, such as a dental fixture, intended for implantation may alone be referred to as an implant even if other parts are to be connected thereto.

By "biocompatible" is meant a material or object which, upon contact with living tissue, does not as such elicit an adverse biological response (for example inflammation or other immunological reactions) of the tissue.

By "non-bioresorbable" is meant a material or object which is not completely chemically and/or biologically degraded after insertion into a living body, even within a period of up to several years. A non-bioresorbable medical device may contain substances to be released into the body of a patient after implantation, but in such cases the general structure of medical device remains intact. For example, any medical device comprising a metallic or ceramic substrate is non-bioresorbable.

By "soft tissue" is meant any tissue type, in particular mammalian tissue types, that is not bone or cartilage. Examples of soft tissue for which the present medical device is suitable include, but are not limited to, connective tissue, fibrous tissue, epithelial tissue, vascular tissue, muscular tissue, mucosa, gingiva, and skin.

By "nanoparticles" is here meant particles having an average particle size of 500 nm or less, typically as measured with transmission electron microscopy (TEM) or Dynamic Light Scattering (DLS).

The medical device according to the present invention typically comprises a substrate having a surface intended to contact living tissue, and at least part of the surface comprises nanoparticles as described herein.

In embodiments of the invention, the substrate may comprise a metallic material.

Typically, the substrate comprises a body at least partly formed of the metallic material. The metallic material may be selected from titanium, zirconium, hafnium, vanadium, niobium, tantalum, cobalt and iridium, and alloys thereof. A surface of the substrate that is in contact with the nanoparticles may for example comprise titanium oxide, in particular in embodiments where the substrate comprises or is formed of titanium. In such embodiments, the titanium oxide may be the native titanium oxide that naturally and instantaneously forms on a titanium surface upon contact with oxygen, e.g. in air. In embodiments where the substrate comprises or is formed of another metallic material mentioned above, a surface thereof that is in contact with the nanoparticles typically comprises a native oxide of the respective metal mentioned above.

In other embodiments, the substrate may comprise a non-metallic material, such as a biocompatible ceramic material, for example zirconia, or a biocompatible polymeric material. Suitable materials are known to those skilled in the art. In such embodiments, the substrate may be formed of a ceramic body, or of a body of polymeric material. In the case of a polymeric material, it is typically, but not necessarily, non-biodegradable.

The nanoparticles may comprise bismuth, elemental or in the form of a compound, or a gallium compound. Typically the nanoparticles comprise at least one of gallium oxide, gallium nitride, bismuth oxide, bismuth nitride, elemental bismuth, and combinations of these materials with other elements, typically metals.

For instance, the nanoparticles may be metal nanoparticles, e.g. bismuth nanoparticles, or gallium and/or bismuth mixed with one or more other metals. Alternatively the nanoparticles may be metal oxide nanoparticles, e.g. gallium oxide nanoparticles or bismuth oxide nanoparticles, or mixed metal oxide nanoparticles (incorporating at least one of bismuth and gallium), e.g. bismuth or gallium doped titanium oxide nanoparticles. Alternatively the nanoparticles may be metal nitride nanoparticles, e.g. gallium nitride nanoparticles.

A single nanoparticle may essentially consist of elemental post-transition metal, in particular elemental bismuth, or a compound of a non-toxic post-transition metal, such as a gallium or bismuth compound, for example gallium oxide, gallium nitride, bismuth oxide or bismuth nitride. "Essentially consist" here means that nanoparticles consist of the element or compound, but allows minor amounts of impurities, e.g. by copper, silicon etc., which may be present at a total content of up to e.g. 10 at %, such as up to 5 at %, or up to 2 at % and typically at less than 1 at %, based on the chemical composition of the nanoparticles. Hence, in embodiments where the nanoparticles essentially consist of a non-toxic post-transition metal or a compound of a non-toxic post-transition metal, such as bismuth or a bismuth compound or a gallium compound, the content of the non-toxic post-transition metal or compound of non-toxic post-transition metal is at least 90 at % (including the elements) other than non the-toxic post-transition metal in the case of a compound), typically at least 95 at %, and more preferably at least 98 at % or even 99 at %. "Impurities" here refers to undesired elements and compounds contained in the nanoparticle. Such impurities may not be removable by simple cleaning. In contrast, surface contamination e.g. by carbon, which may be removed by cleaning the nanoparticle and keeping it under a controlled atmosphere, for example in water, is not considered to be an impurity within the definition above. Carbon contamination of the nanoparticle surface may result in high atomic concentrations of carbon (e.g. up to 30 at %); the nanoparticles may still however essentially consist of said the non-toxic post-transition metal or 'compound of a non-toxic post-transition metal.

In some embodiments, a single nanoparticle may comprise more than one non-toxic post-transition metal, for example both bismuth and gallium, and/or in the form of nitride as well as oxide. In other embodiments, nanoparticles essentially consisting of either gallium oxide, gallium nitride, elemental bismuth, bismuth oxide or bismuth nitride may be used in combination with at least one other type of nanoparticles consisting of another one of gallium oxide, gallium nitride, elemental bismuth, bismuth oxide or bismuth nitride. Nanoparticles essentially consisting of one of the bismuth or gallium compounds may also be mixed with nanoparticles comprising both bismuth and gallium in a single nanoparticle.

In general, the at least one non-toxic post-transition metal, in particular gallium and/or bismuth, may be present in the nanoparticles typically at a content in the range of from 5 at % to 50 at %, for example from 10 at % to 50 at % or from 10 at % to 40% or from 15 at % to 40 at %. In the case of using elemental bismuth, the bismuth content of the nanoparticles may be in the range of from 5 at % to 100 at %.

In further embodiments of the invention, a single nanoparticle may comprise titanium or a titanium compound (e.g. oxide or nitride) in addition to gallium and/or bismuth. In such embodiments, the gallium or bismuth content of the nanoparticles may be low, for example from 5 to 15 at %.

It is also contemplated that one or more additional types of nanoparticles may be used in combination with one or more types of gallium- or bismuth-containing nanoparticles;

in one embodiment, additional nanoparticles comprising or essentially consisting of for example a metal or metal compound may be used. Preferred examples include titanium compounds such as titanium oxide and titanium nitride.

A surface layer of applied nanoparticles may have an atomic content of bismuth and/or gallium in the same ranges as indicated above for the nanoparticles as such. Hence, a medical device may comprise a substrate with a surface layer having a content of gallium and/or bismuth in the range of from 5 at % to 50 at % (up to 100% in the case of nanoparticles consisting of elemental bismuth), for example from 10 at % to 50 at % or from 10 at % to 40% or from 15 at % to 40 at %.

The nanoparticles according to embodiments of the invention typically have an average particle size of 500 nm or less. In embodiments of the invention, the nanoparticles may have an average particle size of 300 nm or less, 200 nm or less, 100 nm or less, 50 nm or less, such as 30 nm or less. For example, the average particle size may be in the range of from 10 to 500 nm, such as from 20 to 300 nm, from 50 to 250 nm or from 50 to 200 nm.

In embodiments of the invention the nanoparticles may have a size distribution such that at least 50% of the particles have an average particle size in the range of from 50 nm to 250 nm.

In one embodiment according to the present invention, the medical device is a dental abutment intended for insertion at least partially into gingival tissue. The abutment comprises a substrate body having an outer surface. At least part of the outer surface is intended for contact with the gingival tissue (soft tissue contact surface) and comprises nanoparticles as described herein. The nanoparticles present on the surface may give the surface a colored appearance which may desirable in particular for dental applications. The color of a deposited layer of nanoparticles may depend on the layer thickness.

By applying a thin, relatively homogeneous layer of nanoparticles onto the surface of the medical device, different surface properties may be obtained compared to when applying a non-particular layer or coating of the same chemical composition and crystallinity for which bulk material properties are more dominating. It has for example been shown that small nanoparticles have higher surface charge compared to larger analogs (Zareen Abbas, Christophe Labbez, Sture Nordholm, and Elisabet Ahlberg., J. Phys. Chem. C 2008, 112, 5715-5723). It is believed that this may influence the apatite formation as well as adsorption of proteins and cells onto a surface coated with such nanoparticles.

Typically the nanoparticles have a substantially spherical shape, although a somewhat irregular morphology is likely.

In embodiments of the invention where the gallium and/or bismuth is present as an oxide, the oxide may be at least partly crystalline.

The nanoparticles may provide a nanoporous layer on the surface of the medical device. The nanoparticles may be closed packed together on the surface, resulting in a layer with an inherent porosity ranging from 0.225*R for monolayers or from 0.732*R for multilayers, respectively, R being the radius of the nanoparticles. A multilayer, i.e. a layer comprising more than one nanoparticle in a direction normal to the surface in which the nanoparticles are present, may have higher porosity due to mismatch in the packing of the nanoparticles. The porous nature of the layers result in a larger developed interfacial area compared to a surface without the nanoparticles. Moreover, the nanoparticles also provide a larger electrochemically active surface area, since an electrolyte can penetrate into the porous structure. Thus, the nanoparticle structure, which forms an external surface of the medical device, may be more reactive and may have different electronic properties compared to a surface without the nanoparticles, or a surface having a coating of particles of larger size than the nanoparticles used in the present invention.

Furthermore, it has also been found that the electronic properties of an oxide film covering a bone implant surface have larger effects on the cellular attachment and apatite nucleation than a small change in topography and that a less insulating oxide film may be preferable e.g. for titanium dental implants. Furthermore, a layer of nanoparticles as used in embodiments of the present invention may have such small porosity that it does not allow bacteria to penetrate into and/or accumulate within the layer.

As mentioned above, in some embodiments the surface may further comprise nanoparticles comprising another metal or metal compound, in addition to the nanoparticles comprising gallium and/or bismuth. Said another metal or metal compound may be titanium dioxide. The titanium oxide may consist mainly of anatase (at least 50% anatase). However, also other metal oxides may be used, optionally in combination with titanium dioxide. In embodiments of the invention, the additional nanoparticles may comprise i) nanoparticles consisting essentially of titanium dioxide, and optionally also ii) nanoparticles consisting essentially of an oxide of one or more of zirconium, hafnium, vanadium, niobium, tantalum, cobalt and iridium, oxides of zirconium and/or iridium being particularly advantageous. Mixing titanium nanoparticles with nanoparticles of one or more of the above oxides, various properties of the resulting layer may be obtained e.g. with respect to color, strength and/or electronic properties. For example, in combination with nanoparticles of titanium dioxide, nanoparticles of iridium oxide may be used to enhance the electronic properties of the layer. Preparation of titanium oxide nanoparticles, as well as characterization and deposition thereof, is described in non-published European Patent Application No. 11165686.4, filed 11 May 2011, hereby incorporated by reference.

In embodiments of the invention, the nanoparticles form a layer on at least a part of the surface of the medical device. Thus, since the surface of the medical device is intended for contact with living tissue, the nanoparticles are intended to be in contact with living tissue, in particular bone or soft tissue.

In embodiments of the invention, the layer formed by the nanoparticles may have a thickness in the range of from 8 nm to about 1 µm, typically from 50 nm to 500 nm, for example from 100 nm to 400 nm. Thin layers are advantageous because of better adherence to the substrate surface. Also, in the case of a sintered layer (see below) of nanoparticles, such thin layers may have higher strength than thicker layers. The layer may be a monolayer of the nanoparticles. Thus, the lower limit of layer thickness is about the same as the size of the nanoparticles. A thin layer of nanoparticles will reduce the surface roughness on the sub-micrometer level, while preserving the surface roughness on a larger scale (blasting level). Such a surface topography may be beneficial with respect to the long term osseointegration of a bone implant.

In embodiments of the invention, the layer of nanoparticles may have an average surface height ($S_a$) in the range of from 5 nm to 150 nm, for example from 5 to 50 nm.

The layer may be a continuous layer of nanoparticles, which layer may cover at least part of the surface. By "continuous layer" is meant a coherent layer forming a single area. Contrary to a continuous layer, a discontinuous layer would be formed of multiple separate layer areas. In embodiments of the invention, the nanoparticles may form a layer which completely covers the surface of the medical device.

In embodiments of the invention, the nanoparticles are homogeneously distributed throughout the layer.

In embodiments of the invention, the nanoparticles may be sintered. Careful sintering of a layer of the nanoparticles may improve the attachment of the nanoparticles to the substrate. Sintering of the nanoparticles may result in a ceramic or ceramic-like layer. However, the nanoparticles may also be non-sintered.

The nanoparticles comprising bismuth and/or gallium may be produced by known methods. Preparation of monodisperse bismuth nanoparticles is described in Yu et al, J Am Chem Soc (2001) 123: 9198-9199. Preparation of gallium oxide nanoparticles is described in Krajczyk et al, J Microscopy (2006) 223: 231-233, and preparation of monodisperse bismuth oxide nanoparticles is described in Li et al, Mater Chem Phys (2006) 99: 174-180. Preparation of bismuth doped titanium oxide nanoparticles is described in Lv et al, J Hazardous Mater (2009) 161: 396-40. Preparation of gallium nitride nanoparticles is described in Nyk et al, Mater Sci Semicon Proces (2005) 8: 511-514. Gallium and/or bismuth precursors used in the above references include $Ga_2O_3$, $Bi(NO_3)_3$, $BiCl_3$, and $Bi—[N(SiMe_3)_2]_3$.

The medical device according to embodiments of the invention may be obtained by
 a) providing a biocompatible substrate having a surface;
 b) providing a dispersion of nanoparticles comprising a non-toxic post-transition metal, which nanoparticles have an average particle size of less than 500 nm, which nanoparticles are dispersed in a solvent; and
 c) applying the dispersion of nanoparticles onto the surface of the substrate.

In particular, the nanoparticles may comprise a compound of a non-toxic post-transition metal as described above, in particular an oxide or a nitride of a non-toxic post-transition metal, such as an oxide or a nitride of gallium and/or bismuth as described above.

Typically, the nanoparticles have an average particle size of 100 nm or less, e.g. 50 nm or less, or 30 nm or less.

In the dispersion provided in step b), the nanoparticles may be completely dispersed, also referred to as "monodisperse" or "monodispersed". In such embodiments, in step c) each nanoparticle present in the dispersion will be applied on the surface individually. However, once applied onto the substrate surface, the nanoparticles are packed closely together to form a closely packed structure.

The solvent may be an aqueous solvent, for example deionized water.

In embodiments of the invention, the dispersion of nanoparticles of metal oxide may be produced by:
 b-i) performing controlled hydrolysis of a gallium and/or bismuth precursor to obtain a colloid dispersion; and
 b-ii) performing dialysis of the colloidal dispersion.

Step b-i) is typically performed by slow, e.g. dropwise, addition of the precursor to deionized water. The hydrolysis of the precursor may be performed with process parameters (e.g. temperature, concentration, pH, time) adjusted according to known chemical principles in order to obtain a desirable result.

The dispersion may be applied on the substrate by any suitable method, including spin coating, spray coating, dipping, immersion, sol-gel coating, electrophoretic deposition, etc.

In embodiments of the invention, the method further comprises allowing the solvent to evaporate after application of the dispersion.

Optionally, the method may further comprise the step of sintering the nanoparticles. In embodiments of the invention, a two step procedure may also be used in which a first layer of the nanoparticles is applied and sintered, and followed by application of further nanoparticles of metal oxide as described herein, which are not sintered. Thus, the benefits of both sintered and of non-sintered nanoparticles may be obtained.

In embodiments of the invention the surface of the substrate may be subjected to a roughening surface treatment prior to step c). Examples of roughening treatment include abrasive blasting and chemical etching. Alternatively, the substrate may be turned, or subjected to a non-roughening treatment, such as polishing.

EXAMPLES

Example 1. Production

Coins of commercially pure (cp) titanium (grade 4) were manufactured and cleaned before spin coating with nanoparticles of bismuth oxide ($Bi_2O_3$). Bismuth nanoparticles (product name BI-OX-03-NP.200N, American Elements, USA) were dispersed in acetate buffer pH 5.0. Cleaned coins were mounted on a rotatable electrode. The speed of electrode rotation was increased and the coins were immersed in acetate buffer containing bismuth oxide nanoparticles for 5 seconds. The speed of rotation decreased to 0 rpm and the coins were immersed in a beaker with deionized water for 5 seconds to remove the remaining unbound bismuth nanoparticles on the surface. The coins were dried and were thereafter packaged in plastic containers, and sterilized with electron beam irradiation.

Example 2. Surface Characterization

For all surface characterization experiments, specimens of commercially pure (cp) titanium and specimens spin coated with bismuth nanoparticles produced as described in Example 1 were used.

2a) Surface Morphology and Surface Chemistry

Surface morphology and surface chemistry analyses were performed with environmental scanning electron microscopy (XL30 ESEM, Philips, Netherlands)/energy dispersive spectroscopy (Genesis System, EDAX Inc., USA) at an acceleration voltage of 30 kV and 10 kV for surface morphology and surface chemistry, respectively.

Figure 1A:
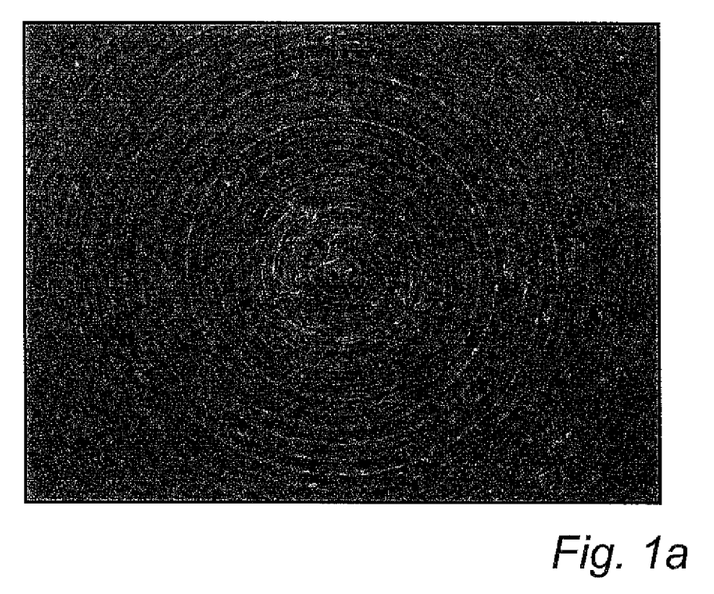
FIG. 1a-b are scanning electron microscopy (SEM) images of different magnifications showing a substrate surface without nanoparticles.
Figure 1B:
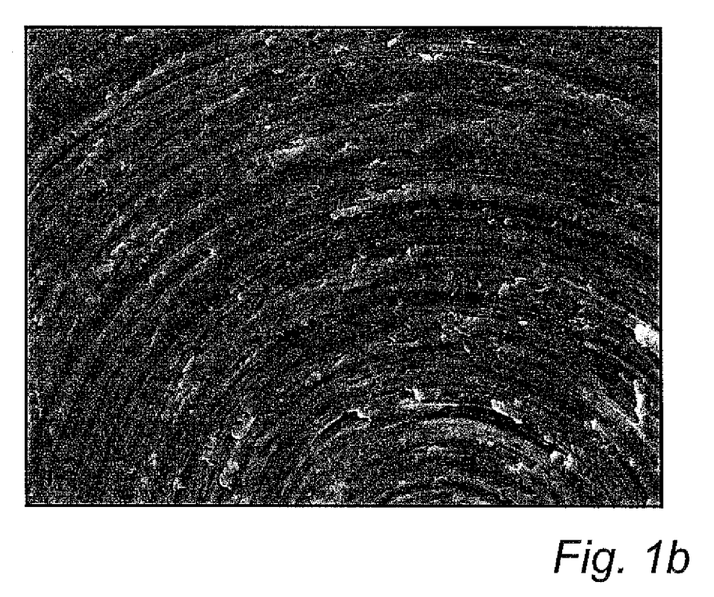
Figure 2A:
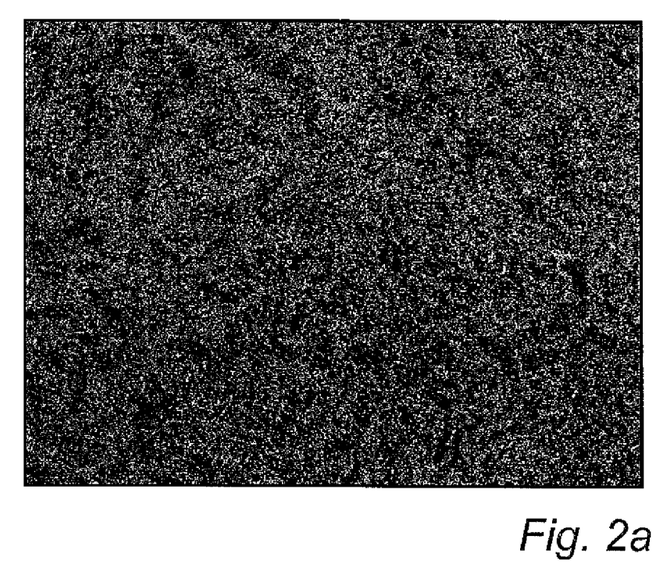
FIG. 2a-b are scanning electron microscopy (SEM) images of different magnifications showing a substrate surface coated with bismuth oxide nanoparticles according to embodiments of the invention.
Figure 2B:
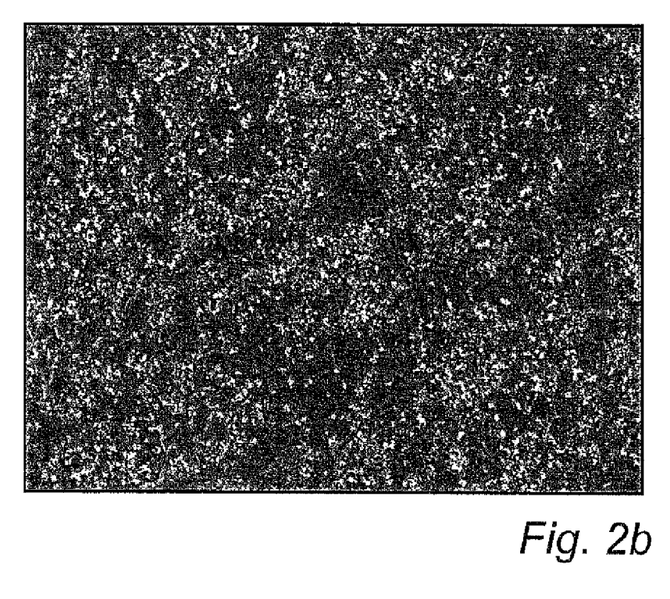

FIGS. 1a and 1b show an uncoated specimen at 100× (FIG. 1a) and 500× (FIG. 1b) magnification, respectively. Machining tracks can be seen, but no particles. In contrast, FIGS. 2a and b show a coated specimen at the same magnifications. As can be seen in FIGS. 2a-b, the coated specimens were partly, but not completely, covered by dispersed nanoparticles.

Figure 3:
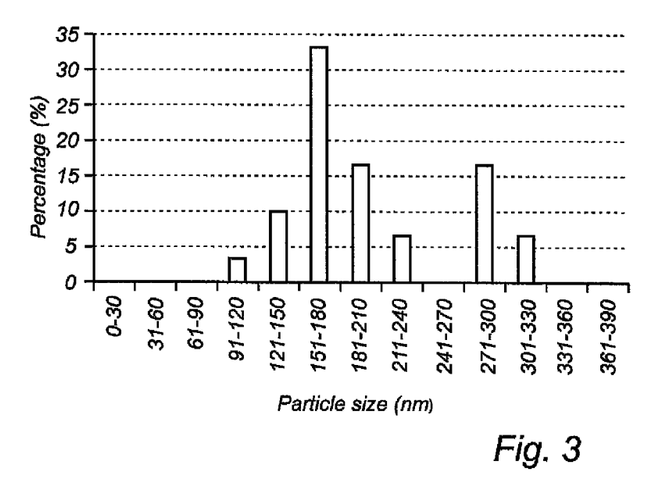
FIG. 3 is a graph presenting the particle size distribution of bismuth oxide nanoparticles used in embodiments of the invention.

The diameter of the $Bi_2O_3$ particles present on the specimen surface was measured and the results are summarized in Table 1. The particle size distribution is also shown in FIG. 3. Due to limited resolution of the technique used, nanoparticles smaller than 115 nm are difficult or impossible to detect and measure. Thus, although the minimum nanoparticle size measured was 115 nm in this example, the presence of smaller nanoparticles cannot be excluded.

TABLE 2

Particle size of $Bi_2O_3$ nanoparticles, measured with SEM (n = 30)
Diameter of $Bi_2O_3$ nanoparticles (nm)

| Mean | Standard deviation | Min | Max |
|---|---|---|---|
| 208 | 63 | 115 | 330 |

Concentrations of bismuth (Bi) on the $Bi_2O_3$ spin coated specimens were analyzed to be up to 5.1 atomic % (at %). Bi concentrations in the bismuth nanoparticles were analyzed to be up to 43.9 at % (see Table 2). Other elements detected were titanium (Ti) and oxygen (O). The analytical depth with this technique is estimated to be approximately 1 µm, i.e. deeper than the nanoparticle layer thickness.

TABLE 2

Surface chemistry analyses with EDS of uncoated and spin coated specimens, respectively. FIGURES are mean values (n = 9), standard deviations within parentheses.

| | Specimen surface type | | |
|---|---|---|---|
| | | Bismuth nanoparticles spin coated (at %) | |
| Elements | Ti (uncoated)* (at %) | Analysis area approximately 15 × 10 µm | Analysis when zooming on nanoparticles |
| Bi | — | 2.0 (1.6) | 30.8 |
| Ti | 100 (0.0) | 98.3 (1.1) | 24.3** |
| O | — | — | 44.9 |

*When analyzed with EDS the instrument suggested 10.6 at % N and 89.4 at % Ti because the excitation energy for Ti La (electron shell) and N Ka (electron shell) are very close 0.45 keV respectively 0.38 keV, but the uncoated titanium specimens do not consist of nitrogen.
**The analytical depth with this technique is estimated to be approximately 1 µm, i.e. deeper than the diameter of the bismuth nanoparticle; hence the Ti of the specimen body (the substrate) is detected also.

Example 3. Antimicrobial Effect a) Inhibition of Bacterial Growth Using Film Contact Method A film contact method as described in M. Yasuyuki, K. Kunihiro, S. Kurissery, N. Kanavillil, Y. Sato, Y. Kikuchi. *Biofouling* 26 (2010) 851-858, was used for evaluating the antimicrobial effect. Streak plates of *Pseudomonas aeruginosa* (PA01) were made and 1 colony was inoculated to 5 ml tryptic soy broth (TSB) in culture tubes and grown under shaking conditions for 18 hours. Cell density was measured in a spectrophotometer at OD 600 nm and counted using a cell counting chamber. The cell culture was adjusted with sterile TSB to 1-5×10$^6$ cells/ml. Specimens of commercially pure (cp) titanium coins (diameter of 6.25 mm) and cp titanium coins spin coated with $Bi_2O_3$ nanoparticles according to Example 1 above were aseptically prepared and placed each in a respective well of a 12 well plate. Thin transparent plastic film was punched, and sterilized using 70% ethanol and UV irradiation on each side. A 15 µl drop of bacteria in TSB was applied on each specimen. One thin plastic film per specimen was placed over the bacteria on the specimens so that the bacterial solution was evenly spread over the specimen surface, ensuring good contact. After incubation for 24 hours at 35±2° C., the film of each specimen was aseptically removed and washed by pipetting 1 ml PBS over the surface into a separate 2 ml eppendorf tube per specimen. The specimens were transferred to the same eppendorf tubes as used when washing the film. First each specimen surface was washed by pipetting the very same PBS as the film was previously washed with. Next, the specimens were sonicated and for 1 minute and vigorously vortexed for 1 minute in the very same tube as previously used when washing the film. Serial dilutions and plate count were performed. Plates were incubated for 24 hours and colony numbers counted and recorded. The $Bi_2O_3$ spin coated titanium coins exhibited a weak antibacterial effect against PA01 compared to uncoated titanium, see Table 3.

TABLE 3

Antibacterial activity was calculated as percent reduction after 24 hours incubation of test specimen against *P. aeruginosa* (PA01).

| Test specimens | Reduction of PA01 (%) |
|---|---|
| Uncoated titanium | 2% |
| $Bi_2O_3$ spin coated titanium | 19% |

The person skilled in the art realizes that the present invention by no means is limited to the preferred embodiments described above. On the contrary, many modifications and variations are possible within the scope of the appended claims.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A medical device, which is a dental implant intended for implantation at least partially into living tissue, said dental implant comprising a non-bioresorbable substrate having a surface intended for contact with living tissue, wherein the surface includes a homogenous monolayer of nanoparticles comprising titanium dioxide, bismuth nitride, and gallium nitride, the monolayer of nanoparticles having a thickness from 100 nm to 400 nm with said nanoparticles having an average particle size of 500 nm or less.

2. The medical device according to claim 1, wherein said nanoparticles of titanium dioxide have an average particle size of 100 nm or less.

3. The medical device according to claim 1, wherein said medical device comprises a substrate having said surface, which substrate comprises a metal or an alloy.

4. The medical device according to claim 3, wherein said substrate comprises titanium, zirconium, hafnium, vanadium, niobium, tantalum, cobalt or iridium, or an alloy thereof.

5. The medical device according to claim 1, wherein the dental implant is a dental fixture intended to be inserted at least partially into living bone tissue.

6. The medical device according to claim 1, wherein the dental implant is a dental abutment, intended to be in contact with living soft tissue.

7. A method of implanting a medical device into the living body of a human or animal, the method comprising:
    a) providing a medical device according to claim 1; and
    b) implanting said medical device into said living body of a human or animal, wherein the medical device is positioned such that at least part of the surface comprising nanoparticles comprising a non-toxic post-transition metal is in contact with living tissue.

* * * * *